United States Patent
Wieser et al.

(10) Patent No.: US 9,440,924 B2
(45) Date of Patent: Sep. 13, 2016

(54) ACETONE SOLVATE OF IVABRADINE HYDROCHLORIDE

(75) Inventors: Josef Wieser, Kundl (AT); Ulrich Griesser, Innsbruck (AT); Michael Enders, Innsbruck (AT); Volker Kahlenberg, Innsbruck (AT)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 14/236,608

(22) PCT Filed: Jul. 31, 2012

(86) PCT No.: PCT/EP2012/064920
§ 371 (c)(1),
(2), (4) Date: Jun. 16, 2014

(87) PCT Pub. No.: WO2013/017582
PCT Pub. Date: Feb. 7, 2013

(65) Prior Publication Data
US 2014/0336179 A1    Nov. 13, 2014

(30) Foreign Application Priority Data

Aug. 2, 2011 (EP) .................................... 11006336

(51) Int. Cl.
*C07D 223/16* (2006.01)
(52) U.S. Cl.
CPC .................................. *C07D 223/16* (2013.01)
(58) Field of Classification Search
CPC .................................................... C07D 223/16
USPC ...................................... 540/523; 514/212.07
See application file for complete search history.

(56) References Cited

U.S. PATENT DOCUMENTS

| 7,384,932 B2 | 6/2008 | Horvath et al. |
| 7,867,997 B2 | 1/2011 | Horvath et al. |
| 2005/0228177 A1 | 10/2005 | Lerestif et al. |
| 2006/0194962 A1 | 8/2006 | Horvath et al. |
| 2006/0194963 A1 | 8/2006 | Horvath et al. |
| 2006/0194964 A1 | 8/2006 | Horvath et al. |
| 2006/0194965 A1 | 8/2006 | Horvath et al. |
| 2007/0082886 A1 | 4/2007 | Horvath et al. |
| 2009/0318419 A1 | 12/2009 | Horvath et al. |
| 2009/0318420 A1 | 12/2009 | Horvath et al. |

FOREIGN PATENT DOCUMENTS

| EP | 2 388 248 A1 | 11/2011 |
| WO | WO 2005/110993 A1 | 11/2005 |
| WO | WO 2006/092491 A1 | 9/2006 |
| WO | WO 2006/092492 A1 | 9/2006 |
| WO | WO 2006/092493 A1 | 9/2006 |
| WO | WO 2006/092494 A1 | 9/2006 |

(Continued)

OTHER PUBLICATIONS

ICH Harmonised Tripartite Guideline, Impurities: Guideline for Residual Solvents, ICH Steering Committee, 1997, pp. 1-19.

(Continued)

*Primary Examiner* — Bruck Kifle
(74) *Attorney, Agent, or Firm* — Arent Fox LLP

(57) ABSTRACT

The present invention relates to a novel solvate of ivabradine hydrochloride, a process of its preparation and its use for the preparation of specific polymorphic forms of ivabradine hydrochloride.

19 Claims, 1 Drawing Sheet

(56) References Cited

FOREIGN PATENT DOCUMENTS

| WO | WO 2007/042656 A1 | 4/2007 |
| WO | WO 2007/042657 A1 | 4/2007 |
| WO | WO 2008/146308 A2 | 12/2008 |
| WO | WO 2012/025940 A1 | 3/2012 |

OTHER PUBLICATIONS

International Search Report, International Application No. PCT/EP2012/064920 mailing date Nov. 23, 2012.
European communication dated Nov. 28, 2014 regarding EP Application No. 12 740 610.6.
"Solvation", International Union of Pure and Applied Chemistry Compendium of Chemical Terminology (IUPAC), PAC, 1994; 66; 1077, p. 1164.
Masciocchi, "Disclosing the extensive crystal chemistry of Ivabradine hydrochloride, in its pure and solvated phases", Technical Article, Powder Diffraction 28(3), 2013, pp. 200-206.
Third Party Observation for application No. EP20120740610 issued Apr. 6, 2016.
Third Party Observation for application No. EP20120740610 issued Feb. 17, 2016.
Third Party Observation for application No. EP20120740610 issued Feb. 22, 2016.

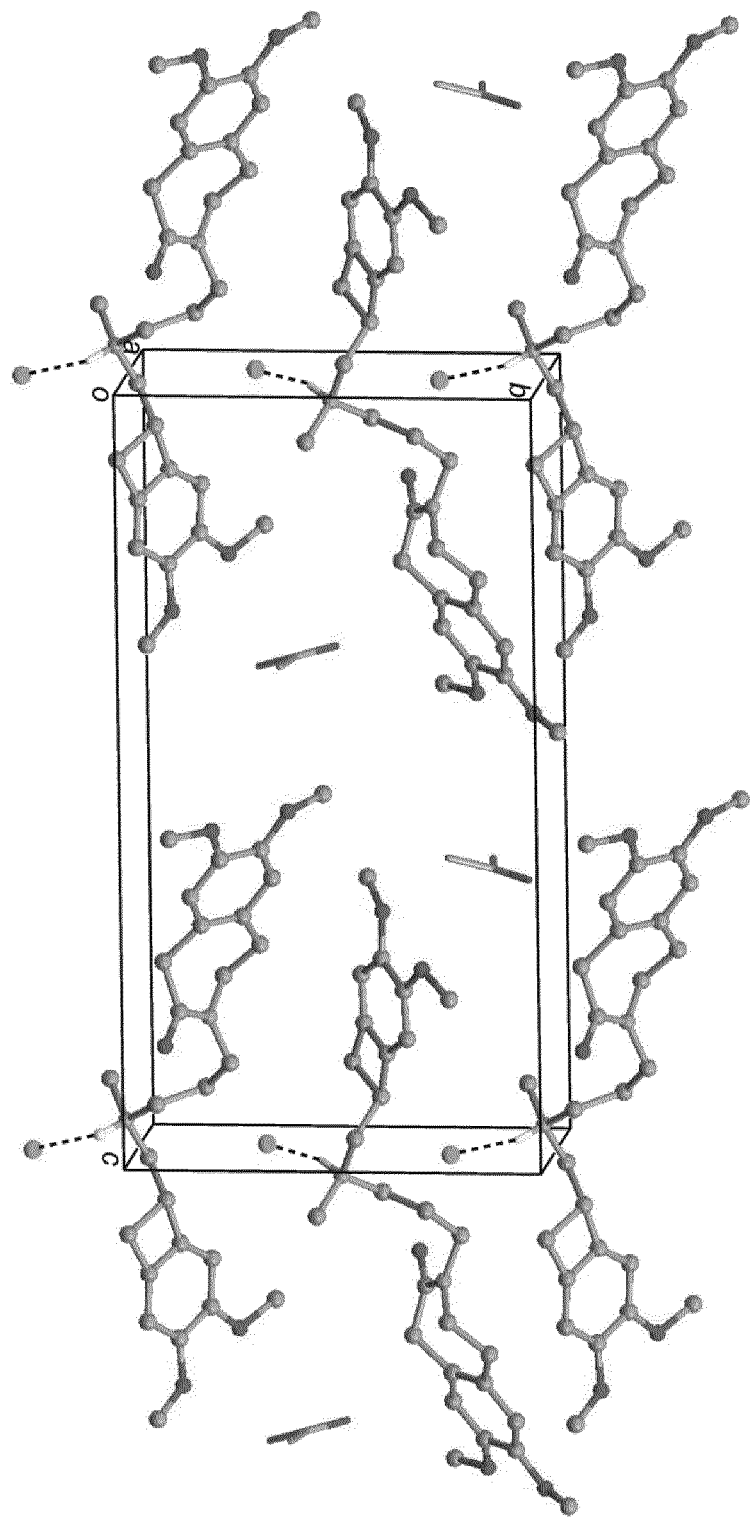

ACETONE SOLVATE OF IVABRADINE HYDROCHLORIDE

CROSS-REFERENCE TO RELATED APPLICATION

This application is a 371 National Stage entry of International Application No. PCT/EP2012/064920, filed Jul. 31, 2012, now WO 2013/017582 with an International Publication date of Feb. 7, 2013, which claims the benefit of priority to EP 11006336.9, filed Aug. 2, 2011, the entire specification, claims and drawings of which are incorporated herewith by reference.

FIELD OF THE INVENTION

The present invention relates to a novel crystalline solvate of ivabradine hydrochloride and a process of its preparation. It further relates to its use for the preparation of specific polymorphic forms of ivabradine hydrochloride. It also relates to a process for the preparation of said specific polymorphic forms of ivabradine hydrochloride, starting from the novel crystalline solvate of ivabradine hydrochloride, and to said specific polymorphic forms as such. Moreover, it relates to pharmaceutical compositions comprising said specific polymorphic forms of ivabradine hydrochloride and specific containers suitable for storing said compositions, preferably for an extended period of time.

BACKGROUND OF THE INVENTION

3-[3-({[(7S)-3,4-dimethoxybicyclo[4.2.0]octa-1,3,5-trien-7-yl]methyl}(methyl)amino)propyl]-7,8-dimethoxy-2,3,4,5-tetrahydro-1H-3-benzazepin-2-one, hereinafter also referred to as ivabradine, is a novel medication used for the symptomatic management of stable angina pectoris. It is marketed under the trade name Procoralan, Coralan in India, Australia or, such as in Italy, Corlentor and was also known as S-16257 during its development. Ivabradine acts by reducing the heart rate in a mechanism different from beta blockers and calcium channel blockers, two commonly prescribed antianginal drugs. It is classified as a cardiotonic agent. The chemical structure of the marketed form, ivabradine hydrochloride, is shown in formula (I):

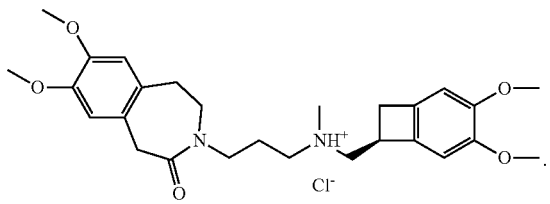

(I)

The polymorphic form δ (hereinunder: delta) of ivabradine hydrochloride and a method for its production is disclosed in U.S. Pat. No. 7,384,932, and the polymorphic form δd (hereinunder: delta-d) of ivabradine hydrochloride is disclosed in U.S. Pat. No. 7,867,997. According to the teaching of these documents, the crystallization of ivabradine hydrochloride is carried out in the solvent acetonitrile, wherefrom, depending on the drying conditions, either polymorphic form delta or polymorphic form delta-d is obtained. Acetonitrile is a class 2 solvent, and its content in pharmaceutical products is limited to 410 ppm (ICH Steering Committee, Guideline for Residual Solvents, 17 Jul. 1997). Therefore, the polymorphic forms delta or delta-d obtainable by crystallization from acetonitrile are not optimal in that they contain residual ICH class 2 solvent to a certain extent.

WO 2008/146308 discloses a process for the preparation of a further polymorphic form of ivabradine hydrochloride, the alpha form. Three concrete possibilities are disclosed how this alpha form can be obtained. First, in example 7, ivabradine hydrochloride is prepared using the well-known solvent acetonitrile. According to this synthesis, a further solvent, ethyl acetate, is necessary to obtain the alpha form. Second, in example 8, the starting material is amorphous ivabradine hydrochloride which has to be prepared in an upstream stage wherein this amorphous form is combined with ethyl acetate as solvent. Third, in order to obtain the alpha form, a process is described which starts with a mandatory heating step according to which ivabradine hydrochloride is taken up in acetone and heated to reflux in order to obtain a clear solution; after this heating stage and an intermediate filtration step, acetone has to be distilled off, i.e. a further heating and concentration step is required.

Polymorphism is a phenomenon relating to the occurrence of different crystal forms for one molecule. Different polymorphs may possess distinct advantageous physical properties such as increased solubility, increased chemical stability, decreased hygroscopicity, increased bulk density, increased photostability, improved processability during formulation and the like. The forms delta and delta-d of ivabradine hydrochloride are valuable polymorphs for the use in pharmaceutical preparations. However, the literature is silent on specific formulations exhibiting suitable conditions for the formulation of forms delta and delta-d of ivabradine hydrochloride.

An object of the present invention was the provision of a novel process for the preparation of polymorphic forms delta and delta-d of ivabradine hydrochloride, in particular form delta. Due to the fact that these polymorphic forms represent valuable products, it was an object that upscaling of this process—in order to meet the needs of industrial-scale production—should be easily accomplishable. It was a further object that the novel process allows for the production of high-purity products which, in particular, should contain as low an amount of possibly harmful compounds as possible.

Surprisingly, it was found that a novel crystalline solvate of ivabradine hydrochloride allows for the realization of this process. It was found that in terms of the starting material from which this solvate can be produced, the novel process is extremely flexible.

Further, it was found that the reaction conditions necessary to produce said crystalline solvate are highly advantageous in terms of energy consumption in combination with the chemical nature of the solvent used.

Yet further, it was found that starting from the novel acetone solvate, in particular the polymorphic forms delta and delta-d of ivabradine hydrochloride can be prepared in a simple and straightforward manner and that these polymorphic forms obtainable via the novel acetone solvate of the present invention are advantageous in that they are free of ICH class 2 solvents.

SUMMARY OF THE INVENTION

Therefore, the present invention relates to a crystalline acetone solvate of the compound of formula (I)

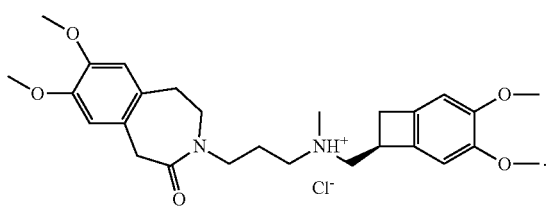

The present invention further relates to a process comprising
a) providing a crystalline compound of formula (I)

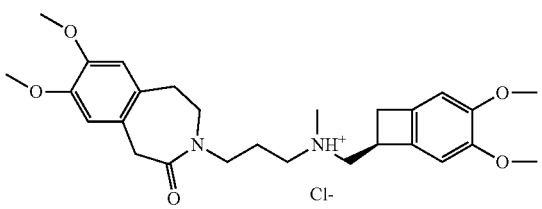

or a solvate, other than an acetone solvate, thereof;
b) combining the compound provided in a) with acetone at a temperature in the range of from 0 to 30° C. and crystallizing the acetone solvate for a time in the range of from 1 to 48 h and at a temperature in the range of from 0 to 30° C.;
c) recovering a crystalline acetone solvate of the compound of formula (I).

The present invention further relates to said process which further comprises a step d-i) of drying the crystalline acetone solvate recovered in c), wherein a crystalline compound of formula (I) is obtained, at least partially having crystalline form delta-d, or a step d-ii) of subjecting the crystalline acetone solvate recovered in c) to an atmosphere having a relative humidity in the range of from up to 50%, wherein a crystalline compound of formula (I) is obtained, at least partially having crystalline form delta.

Further, the present invention relates to a crystalline compound of formula (I), the crystalline compound of formula (I) being obtainable or obtained by a process comprising
a) providing a crystalline compound of formula (I) or a solvate, other than an acetone solvate, thereof;
b) combining the compound provided in a) with acetone at a temperature in the range of from 0 to 30° C. and crystallizing the acetone solvate for a time in the range of from 1 to 48 h and at a temperature in the range of from 0 to 30° C.;
c) recovering a crystalline acetone solvate of the compound of formula (I);
d-i) drying the crystalline acetone solvate recovered in c) to obtain the form delta-d of the compound of formula (I), or
d-ii) subjecting the crystalline acetone solvate recovered in c) to an atmosphere having a relative humidity in the range of from up to 50%, preferably from 30 to 50% to obtain the form delta of the compound of formula (I), said delta-d form or said delta form having an acetonitrile content, preferably an ICH class 2 solvent content of less than 200 ppm, preferably of less than 20 ppm, more preferably of less than 5 ppm.

The present invention further relates to a process for the preparation of a crystalline compound of formula (I)

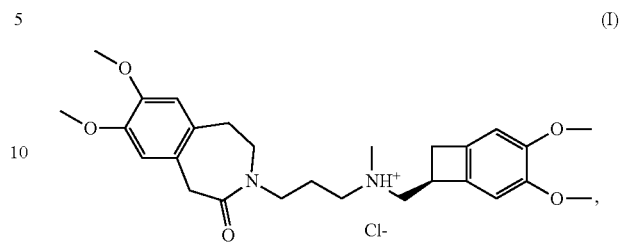

said compound at least partially, preferably essentially completely having polymorphic form delta, said process comprising subjecting a preferably crystalline acetone solvate of the compound of formula (I), preferably the crystalline acetone solvate according as described above, to an atmosphere having a relative humidity in the range of from up to 50%, preferably from 30 to 50%, more preferably from 40 to 50%.

The present invention further relates to a crystalline compound of formula (I)

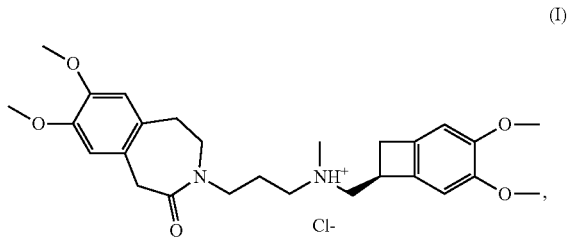

at least partially, preferably essentially completely having crystalline form delta-d and/or delta, preferably delta, said crystalline compound having an acetonitrile content, preferably an ICH class 2 solvent content of less than 200 ppm, preferably of less than 20 ppm, more preferably of less than 5 ppm.

The present invention further relates to the use of an acetone solvate of the compound of formula (I), preferably of a crystalline acetone solvate of the compound of formula (I), more preferably of the crystalline acetone solvate as described above, for the preparation of a crystalline compound of formula (I)

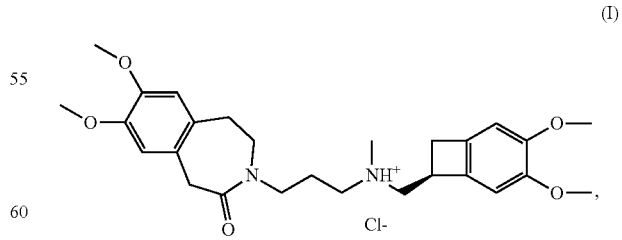

said crystalline compound of formula (I) at least partially, preferably essentially completely having crystalline form delta and/or delta-d, preferably delta.

The present invention further relates to a pharmaceutical composition, comprising the inventive crystalline compounds of formula (I), in particular the inventive crystalline compound of formula (I) having an acetonitrile content, preferably an ICH class 2 solvent content of less than 200 ppm, preferably of less than 20 ppm, more preferably of less than 5 ppm as described above, and at least one pharmaceutically acceptable excipient.

The present invention further relates to a container comprising said pharmaceutical composition, the container containing means for keeping the equilibrium relative humidity of the pharmaceutical composition in a range of from 30 to 50% determined at a temperature of the composition of 25° C., preferably for an extended period of time, more preferably for at least 180 d, more preferably for at least 2 years.

In the context of the present invention the following abbreviations have the indicated meaning, unless explicitly stated otherwise:
XRPD: Powder X-ray diffraction
r.h. or RH: relative humidity
r.t.: room temperature

BRIEF DESCRIPTION OF THE DRAWINGS

FIG. 1 shows the unit cell of the acetone solvate of the compound of formula (I) according to the present invention.

DETAILED DESCRIPTION OF THE INVENTION

The Acetone Solvate

As described above, the present invention relates to a crystalline acetone solvate of the compound of formula (I)

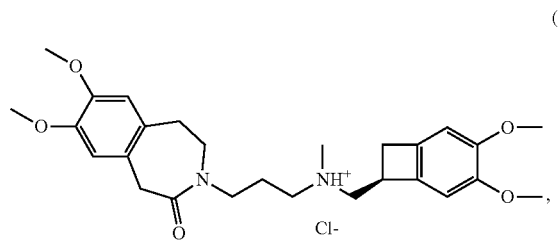

(I)

i.e. an acetone solvate of ivabradine hydrochloride. As to the preparation of this acetone solvate, no specific restrictions exist provided that the crystalline acetone solvate is obtained. Preferably, the acetone solvate is prepared according to a method wherein a specific starting material is provided, said starting material is combined with acetone from which the solvate is formed, the resulting mixture is subjected to crystallization conditions, and the finally obtained crystallized acetone solvate is recovered from the reaction mixture by a suitable method.

A preferred process for preparing the crystalline acetone solvate according to the present invention comprises
a) providing a crystalline compound of formula (I) or a solvate, other than an acetone solvate, thereof;
b) combining the compound provided in a) with acetone and crystallizing the acetone solvate;
c) recovering the crystalline acetone solvate.

As to step a), it is noted that according to a conceivable alternative embodiment, it is also possible to provide, as starting material, a crystalline acetone solvate of the crystalline compound of formula (I). As solvate other than an acetone solvate, hydrates are mentioned by way of example.

Therefore, the present invention also relates to the above-described process, comprising
a) providing a crystalline compound of formula (I) or a hydrate thereof;
b) combining the compound provided in a) with acetone and crystallizing the acetone solvate;
c) recovering the crystalline acetone solvate.

Surprisingly, it was found that there are no restrictions as far as the specific crystalline form of the compound of formula (I) is concerned which is provided in a). In particular, all known crystalline forms of the compound of formula (I) and mixtures of these forms can be employed. Thus, the process for preparing the crystalline acetone solvate of the invention has as an additional advantage a large degree of flexibility with regard to the starting material which is to be employed in the process.

As to these known forms and solvates such as hydrates thereof, reference is made to WO 2005/110993, in particular to the table on page 7 and claim 15, disclosing the alpha form, WO 2006/092493, in particular the table bridging pages 2 and 3, and claim 1, disclosing the beta form, WO 2006/092491, in particular the table bridging pages 2 and 3, and claim 1, disclosing the beta-d form, WO 2006/092492, in particular the table bridging pages 2 and 3, and claim 1, disclosing the gamma form, WO 2006/092494, in particular the table bridging pages 2 and 3, and claim 1, disclosing the gamma-d form, WO 2007/042656, in particular the table bridging pages 2 and 3, and claim 1, disclosing the delta form, and WO 2007/042657, in particular the table bridging pages 2 and 3, and claim 1, disclosing the delta-d form. As to mixtures of two of these forms, the following combinations may be mentioned by way of example: alpha and beta, alpha and beta-d, alpha and gamma, alpha and gamma-d, alpha and delta, alpha and delta-d, beta and beta-d, beta and gamma, beta and gamma-d, beta and delta, beta and delta-d, beta-d and gamma, beta-d and gamma-d, beta-d and delta, beta-d and delta-d, gamma and gamma-d, gamma and delta, gamma and delta-d, gamma-d and delta, gamma-d and delta-d, delta and delta-d. In the same way, mixtures of three different form, four different forms, five different forms, six different forms and seven different forms can be construed from the known forms.

Therefore, the present invention relates to above-described process, wherein in a), the crystalline compound of formula (I) is provided as crystalline form alpha, or beta, or beta-d, or gamma, or gamma-d, or delta, or delta-d, or as a mixture of two or more of these crystalline forms.

Combining the compound provided in a) and acetone can be accomplished by any conceivable method. Depending on the compound provided in a) and the conditions chosen for the combination, dissolving the compound in acetone or suspending the compound in acetone can be mentioned by way of example.

It is also possible to suitably pretreat the compound provided in a), prior to combining it with acetone in b). By way of example, it is possible to subject the compound to a suitable purification and/or washing stage, wherein, for example, acetone is used as washing agent.

In the prior art, as far as the preparation of the alpha form of the compound of formula (I) is concerned, it is disclosed that acetone can be used as solvent for the preparation. It is noted that this prior art does not disclose an acetone solvate and contains no teaching for the skilled person to prepare an acetone solvate, let alone a crystalline acetone solvate. To the contrary, in the prior art acetone is used at elevated temperatures in the preparation of polymorphic form alpha. In particular, the prior art describes that for the preparation of the alpha form, it is mandatory to heat the mixture which results from the combination of the compound of formula (I) and acetone.

Contrary to this teaching, it was found according to the present invention that using acetone at much lower temperatures, preferably at temperatures in the range of at most 50° C., more preferably of at most 40° C., more preferably of at most 30° C., allows for obtaining the novel solvate. No hint is given in the prior art that a combination of low temperatures, temporal constraints and an advantageous solvent acetone could be used. Therefore, the novel process of the present invention, in particular in terms of an industrial-scale production making use of acetone as solvent, allows for decreasing the amount of energy to be employed and to decrease the amount of investments necessary for the process technology. Further, combining and crystallizing is performed at a temperature of at least −10° C., preferably at least −5° C., more preferably at least 0° C. Concerning the time during which crystallization is carried out, no specific restrictions exist provided that the crystalline acetone solvate is obtained in the desired quantity. Preferred crystallization times are in the range of from 0.1 to 96 h, more preferably from 0.5 to 72 h, more preferably from 1 to 48 h.

Therefore, the present invention also relates to above-described process, wherein in b), the compound provided in a) is combined with acetone at a temperature in the range of from 0 to 30° C. and the acetone solvate is crystallized for a time in the range of from 1 to 48 h and at a temperature in the range of from 0 to 30° C.

According to one embodiment of the process of the present invention, combining and crystallizing in b) is performed at a temperature in the range of from 10 to 30° C., preferably from 15 to 30° C., more preferably from 20 to 30° C. such as of from 20 to 25° C. or from 22 to 27° C. or from 25 to 30° C. wherein, during combining and crystallizing, two or more different temperatures or temperature ranges in above-described limits can be realized.

Therefore, the present invention relates to above-described process, wherein in b), combining and crystallizing is performed at a temperature in the range of from 20 to 30° C. According to another embodiment of the present invention, combining and crystallizing in b) is performed at a temperature in the range of from 0 to 30° C. wherein, during combining and/or crystallizing, two or more different temperatures or temperature ranges in above-described limits are realized. Preferably, according to this embodiment, combining in b) is performed at a temperature in the range of from 20 to 30° C. Further preferably, subsequent crystallizing is carried out in at least 2 stages, more preferably in 2 stages wherein during these stages, at least two different temperature ranges are realized. Preferably, a first temperature range (i), subsequent to the combining, is of from more than 10 to 30° C., preferably of from 15 to 30° C., more preferably of from 20 to 30° C., and the second temperature range is of from −10 to +10° C., preferably of from −5 to +10° C., more preferably of from 0 to +10° C. In all crystallizing stages, in particular in the two stage (i) and (ii), the crystallization mixture can be stirred. It is preferred that stirring the mixture is performed in the stages carried out at higher temperatures, preferably in stage (i) whereas in the stages carried out at lower temperatures, preferably in stage (ii), it is preferred to avoid stirring. Generally, there are no specific restrictions as to the time periods during which the different crystallization stages are performed. Preferably, concerning the 2 stages (i) and (ii), it is preferred to perform stage (i) for a time in the range of from 0.05 to 48 h, more preferably of from 0.2 to 12 h, more preferably of from 0.5 to 6 h, and to perform stage (ii) for a time in the range of from 0.05 to 48 h, more preferably of from 0.3 to 60 h, more preferably of from 0.5 to 42 h Therefore, the present invention also relates to above-described process wherein in b), the crystallizing is performed according to a method comprising
(i) stirring the compound provided in a) combined with the acetone for a time in the range of from 0.5 to 6 h and at a temperature in the range of from 20 to 30° C.;
(ii) keeping the mixture obtained from (i) for a time in the range of from 0.5 to 42 h at a temperature in the range of from 0 to 10° C.

Either during combining the compound provided in a) with acetone, or during crystallizing, or during combining and crystallizing, it is possible to suitably seed the crystallization mixture. It was found that seeding is not necessary to prepare the inventive acetone solvate. Therefore, the present invention also relates to above-described process, wherein for crystallizing the acetone solvate of the compound of formula (I), no seeding material is added to the crystallization mixture.

After crystallization, the mixture, usually obtained as suspension of the acetone solvate in its mother liquor, is subjected to separating the crystalline acetone solvate, thereby recovering the crystalline acetone solvate. Generally, there are no specific restrictions as to the suitable methods of separating the crystalline acetone solvate from the mother liquor. Preferably, simple methods such as filtration or centrifugation, more preferably filtration, are employed.

Compared to the prior art process relating to the use of acetone for the preparation of the alpha form of the compound of formula (I), a further advantage of the present invention is the fact that no concentration step via distilling-off surplus acetone is necessary. Quite to the contrary, it is preferred that the crystalline acetone solvate is recovered by simple means such as filtration. By way of example, also centrifugation or the like can be mentioned as conceivable simple methods.

Therefore, the present invention also relates to above-described process, wherein in c), the crystalline acetone solvate is recovered by filtration.

Subsequently, the recovered crystalline acetone solvate can be subjected to one or more suitable washing stages wherein between 2 consecutive washing stages, a filtration stage or the like can be performed.

It is a further advantage of the present invention that the compound provided in a) has to be combined with one advantageous solvent only. In particular, no solvent exchange is necessary in order to prepare the novel solvate of the compound of formula (I).

Therefore, the present invention also relates to above-described process wherein before or during b), the compound provided in a) is combined with no compound other than acetone.

Generally, the present invention also relates to an acetone solvate of the compound of formula (I) which solvate is obtainable or obtained by a process as described above.

The acetone solvate of the present invention, in particular the acetone solvate prepared according to the above-described novel process, preferably contains of from 0.7 to 1.1 mol acetone, more preferably of from 0.8 to 1.1 mol acetone per mol of the compound of formula (I). By way of example, the acetone solvate of the present invention contains of from 0.7 to 0.9 mol or from 0.8 to 1.0 mol or from 0.9 to 1.1 mol acetone per mol of the compound of formula (I).

As mentioned hereinabove, it is preferred that before or during b), the compound provided in a) is combined with no compound other than acetone. Therefore, the compound provided in a) is not contacted with an ICH class 2 solvent. Preferably, the compound provided in a) is not contacted with a solvent selected from the group consisting of acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidone, nitromethane, pyridine, sulfolane, tetrahydrofuran, tetralin, toluene, 1,1,2-trichloroethene, xylene and a mixture of two or more thereof. In particular, the compound provided in a) is not contacted with acetonitrile. Thus, preferably, the crystalline acetone solvate of the present invention has an acetonitrile content, preferably an ICH class 2 solvent content of less than 200 ppm, preferably of less than 20 ppm, more preferably of less than 5 ppm.

Further, the crystalline acetone solvate of the present invention is characterized by exhibiting monoclinic unit cells having space group P2$_1$.

Preferably, these monoclinic unit cells are characterized by the following parameters, as determined by X-ray structural analysis:
a=5.72+/−0.05 Angstrom
b=11.82+/−0.05 Angstrom
c=22.03+/−0.05 Angstrom
alpha=90.0°
beta=93.2°+/−0.1°
gamma=90°

In particular, these monoclinic unit cells are characterized by the following parameters, as determined by X-ray structural analysis:
a=5,7195 Angstrom
b=11.8231 Angstrom
c=22.0250 Angstrom
alpha=90.0°
beta=93.18°
gamma=90°

The crystalline acetone solvate of the present invention can be subjected to further reaction stages as described hereinunder. If the solvate is subjected to such further reaction stages immediately after its preparation, it is not necessary to suitably store it. If the solvate has to be suitably stored, such storing can be easily accomplished by keeping the solvate in an acetone atmosphere at suitable pressure and temperature, preferably at ambient conditions.

Preferred Uses of an Acetone Solvate of the Compound of Formula (I)

Preferably, the crystalline acetone solvate according to the present invention can be used, for example, for the preparation of one or more polymorphic forms of the compound of formula (I). Depending on the conditions the inventive crystalline acetone solvate is subjected to, one specific polymorphic form or a mixture of two or more polymorphic forms may be obtained. According to a preferred embodiment of the present invention, either the delta form or the delta-d form or a mixture of the delta form and the delta-d form of the compound of formula (I) is prepared from the inventive acetone solvate. Moreover, it is noted that such use is not necessarily restricted to crystalline solvates according to the present invention. Generally, it is also conceivable that any kind of acetone solvate of the compound of formula (I) can be used.

Therefore, the present invention relates to the use of an acetone solvate of a crystalline compound of formula (I) for the preparation of a crystalline compound of formula (I)

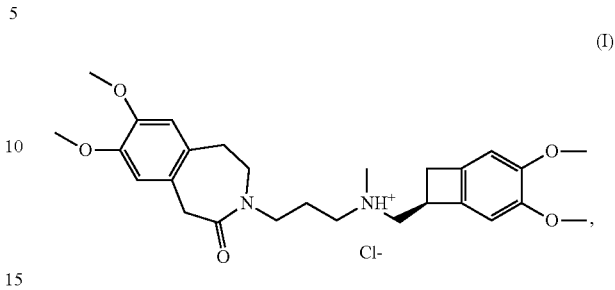

(I)

said crystalline compound of formula (I) at least partially having crystalline form delta and/or delta-d. Preferably, said crystalline compound of formula (I) essentially completely has crystalline form delta and/or delta-d. More preferably, said crystalline compound of formula (I) essentially completely has crystalline form delta. The term "at least partially having crystalline form delta-d" as used in this context of the present invention refers to a crystalline compound of formula (I) wherein more than 50% of the crystalline compound are present in the delta-d form. The term "essentially completely having crystalline form delta-d" as used in this context of the present invention refers a crystalline compound of formula (I) wherein at least 90%, more preferably at least 95%, more preferably at least 99%, more preferably at least 99.9% of the crystalline compound are present in the delta-d form. In particular, the term "essentially completely having crystalline form delta-d" as used in this context of the present invention refers to an embodiment where the polymorphic form delta-d is the only detectable crystalline form of the compound of formula (I).

The term "at least partially having crystalline form delta" as used in this context of the present invention refers to a crystalline compound of formula (I) wherein more than 50% of the crystalline compound are present in the delta form. The term "essentially completely having crystalline form delta" as used in this context of the present invention refers to a crystalline compound of formula (I) wherein at least 90%, more preferably at least 95%, more preferably at least 99%, more preferably at least 99.9% of the crystalline compound are present in the delta form. In particular, the term "essentially completely having crystalline form delta" as used in this context of the present invention refers to an embodiment where the polymorphic form delta is the only detectable crystalline form of the compound of formula (I). As to the preferred uses of acetone solvates of the compound of formula (I), it is even more preferred that the acetone solvate is a crystalline acetone solvate, with a crystalline acetone solvate having the monoclinic unit cell parameters and/or, preferably and, the acetone contents as described above, and further, having an ICH class 2 solvent as described above, being even more preferred.

Thus according to an especially preferred embodiment, the present invention relates to the use of a crystalline acetone solvate of the compound of formula (I) comprising acetone in the range of from 0.8 to 1.1 mol, per mol of the compound of formula (I), having an ICH class 2 solvent content of less than 5 ppm and exhibiting monoclinic unit cells having space group P2$_1$ and having the parameters a=5.72+/−0.05 Angstrom, b=11.82+/−0.05 Angstrom, c=22.03+/−0.05 Angstrom, alpha=90.0°, beta=93.2+/−0.1°, gamma=90° as determined by X-ray structural analysis, for the preparation of a crystalline compound of formula (I) essentially completely having crystalline form delta.

Inventive Preparation of a Crystalline Compound of Formula (I) Having Form Delta and/or Delta-d According to a Process Comprising Stages a) to c)

According to one embodiment, the present invention relates to above-described process comprising stages a) to c), further comprising d) subjecting the acetone solvate recovered in c) to reaction conditions allowing for obtaining the crystalline compound of formula (I) preferably at least partially having crystalline form delta and/or delta-d.

According to one embodiment of the present invention, the compound of formula (I) is prepared from the crystalline acetone solvate recovered in c), wherein the compound of formula (I) at least partially, preferably essentially completely has form delta-d. Generally, all conceivable methods allowing for obtaining such compound can be carried out. Preferably, such compound is prepared by suitably drying the crystalline acetone solvate recovered in c).

Therefore, the present invention also relates to above-described process, further comprising as step d)

d-i) drying the crystalline acetone solvate recovered in c), wherein a crystalline compound of formula (I) is obtained, at least partially, preferably essentially completely having crystalline form delta-d.

The term "at least partially having crystalline form delta-d" as used in this context of the present invention refers to a crystalline compound of formula (I) wherein more than 50% of the crystalline compound obtained from d-i) are present in the delta-d form. The term "essentially completely having crystalline form delta-d" as used in this context of the present invention refers to a crystalline compound of formula (I) wherein at least 90%, more preferably at least 95%, more preferably at least 99%, more preferably at least 99.9% of the crystalline compound obtained from d-i) are present in the delta-d form. In particular, the term "essentially completely having crystalline form delta-d" as used in this context of the present invention refers to an embodiment where the polymorphic form delta-d is the only detectable crystalline form of the compound of formula (I).

The delta-d form is defined with respect to its crystalline structure, for example, in US 2007/0082886 A1, in the table of page 1, right column. That table discloses that the crystalline form delta-d, when characterized by a powder X-ray diffractogram measured using a PANalytical X'Pert Pro diffractometer together with an X'Celerator detector and expressed in terms of line position (Bragg's angle 2 theta, expressed in degrees), comprises peaks at 2 theta positions of 4.1, 6.8, 8.6, 9.1, 10.9, 11.7, 14.6, 15.3, 16.6, 17.2, 18.1, 19.1, 19.6, 20.1, 20.9, 21.4, 22.1, 22.5, 23.4, 23.9, 24.7, 25.6, 26.2, 26.9, 27.6, 29.1 and 29.5 degrees.

The drying conditions of d-i) can be suitably adjusted. Preferably, drying is carried out at a temperature in the range of from 20 to 100° C., more preferably from 30 to 100° C., more preferably from 40 to 90° C. Even more preferred temperatures are in the range of from 50 to 90° C. or from 60 to 80° C. Yet more preferably, drying in d-i) is performed in vacuo. The term "in vacuo" as used in this context of the present invention relates to a pressure of generally less than 1 bar, preferably less than 500 mbar, more preferably less than 100 mbar.

Therefore, the present invention also relates to above-described process, wherein drying according to d-i) is performed at a temperature in the range of from 20 to 100° C., preferably in vacuo.

Further, drying is preferably performed for a time in the range of from up to 72 h, preferably from 1 to 48 h, more preferably from 1 to 24 h, more preferably from 1 to 18 h, more preferably from 4 to 18 h, more preferably from 6 to 18 h.

Therefore, the present invention also relates to above-described process, wherein drying according to d-i) is performed at a temperature in the range of from 20 to 100° C., preferably in vacuo, for a time in the range of from 1 to 48 h.

According to a preferred embodiment of the present invention, the compound of formula (I) is prepared from the crystalline acetone solvate recovered in c), wherein the compound of formula (I) at least partially, preferably essentially completely has form delta. Generally, all conceivable methods allowing for obtaining such compound can be carried out.

Preferably, such compound is prepared by subjecting the crystalline acetone solvate recovered in c) to an atmosphere having a suitable relative humidity. Preferably, the relative humidity of the atmosphere is in the range of up to 60%, more preferably up to 50%, more preferably in the range of from 10 to 50%, more preferably of from 20 to 50%, even more preferably of from 30 to 50%. More preferably, the relative humidity is in the range of from 40 to 50% such as in the range of from 40 to 45%, 41 to 46%, 42 to 47%, 43 to 48%, 44 to 49%, or 45 to 50%. Most preferably, the relative humidity is in the range of from 41 to 45%.

Drying chambers, such as constant climate chambers, capable of controlling the relative humidity therein are commercially available and can be used for subjecting the crystalline acetone solvate to an atmosphere with the defined relative humidity as described above.

Alternatively, step d) can be performed by storing the crystalline acetate solvate of the present invention from step c), at 25° C. in a dessicator in the presence of a saturated solution of magnesium chloride, sodium iodide or potassium carbonate for a time sufficient to equilibrate the wet crystalline acetone solvate of the present invention with the defined atmosphere of the dessicator. Storage in the presence of a concentrated potassium carbonate solution is preferred, as this is expected to provide an equilibrium relative humidity of about 43%.

Therefore, the present invention also relates to an above-described process, further comprising as step d)

d-ii) subjecting the crystalline acetone solvate recovered in c) to an atmosphere having a relative humidity in the range of from up to 50%, preferably from 30 to 50%, more preferably from 40 to 50%, more preferably from 41 to 45%, wherein a crystalline compound of formula (I) is obtained, at least partially, preferably essentially completely, having crystalline form delta.

The term "at least partially having crystalline form delta" as used in this context of the present invention refers to a crystalline compound of formula (I) wherein more than 50% of the crystalline compound obtained from d-ii) are present in the delta form. The term "essentially completely having crystalline form delta" as used in this context of the present invention refers to a crystalline compound of formula (I) wherein at least 90%, more preferably at least 95%, more preferably at least 99%, more preferably at least 99.9% of the crystalline compound obtained from d-ii) are present in the delta form. In particular, the term "essentially completely having crystalline form delta" as used in this context of the present invention refers to an embodiment where the polymorphic form delta is the only detectable crystalline form of the compound of formula (I).

The delta form is defined with respect to its crystalline structure, for example, in US 2009/0318419 A1, in the table of page 1, right column. That table discloses that the crystalline fform delta of ivabradine hydrochloride, when characterized by a powder X-ray diffractogram measured using a PANalytical X'Pert Pro diffractometer together with an X'Celerator detector and expressed in terms of line position (Bragg's angle 2 theta, expressed in degrees), comprises peaks at 2 theta positions of 4.1, 6.8, 8.4, 10.9, 12.2, 14.3, 14.7, 15.3, 16.3, 16.8, 17.5, 17.9, 19.2, 19.8, 20.4, 21.2, 21.7, 22.2, 22.5, 23.1, 24.8, 25.2, 25.6, 26.7, 27.6, 28.4 and 29.6 degrees.

The skilled person will readily appreciate that there are distinctive peaks that would allow to determine presence or absence of crystalline form delta of Ivabradine hydrochloride in the presence of crystalline form delta-d. For example, a powder X-ray diffractogram measured as described in the above paragraph and showing peaks at many, essentially all or even all listed 2 theta positions characteristic of form delta-d, but not comprising distinctive peaks at 2 theta angles of 8.4, 25.2 and/or 28.4 would be indicative of form delta-d essentially devoid of crystalline form delta.

The skilled person will also readily appreciate that there are distinctive peaks that would allow to determine presence or absence of crystalline form delta-d of Ivabradine hydrochloride in the presence of crystalline form delta. For example, a powder X-ray diffractogram measured as described in the above paragraph and showing peaks at many, essentially all or even all listed 2 theta positions characteristic of form delta, but not comprising distinctive peaks at 2 theta angles of 9.1 and/or 23.9 would be indicative of form delta essentially devoid of crystalline form delta-d.

In an analogous manner, namely by comparing powder X-ray diffraction patterns for the respective polymorphic form and by determining distinctive powder X-ray diffraction peaks for the presence or absence of one polymorphic form in another, the presence or absence of any one of the other exisiting polymorphic forms of ivabradine hydrochloride, e.g. the alpha form, the beta form, the beta-d form, the gamma form, and the gamma-d form in a sample comprising form delta or delta-d can be determined.

The term "relative humidity" as used in this context of the present invention describes the amount of water vapor in a mixture of air and water vapor. It is defined as the partial pressure of water vapor in the air-water mixture, given as a percentage of the saturated vapor pressure under those conditions.

Preferably, subjecting the crystalline acetone solvate recovered in c) to said atmosphere according to d-ii) is performed at a temperature in the range of from 15 to 35° C., more preferably of from 20 to 30° C., such as in the range of from 20 to 25° C. or of from 22 to 27° C. or of from 25 to 30° C., most preferably in the range of from 20 to 25° C. The preferred pressure, at these temperatures, is preferably in the range of from 0.9 to 1.1 bar, more preferably in the range of from 0.95 to 1.05 bar, more preferably in the range of from 0.98 to 1.02 bar.

Preferably, subjecting the crystalline acetone solvate recovered in c) to said atmosphere according to d-ii) is performed for a time in the range of from 1 to 10 d, preferably of from 2 to 8 d, more preferably of from 72 to 168 h, more preferably of from 72 to 120 h.

Subjecting the crystalline acetone solvate recovered in c) to said atmosphere according to d-ii) can be carried out in the presence of at least one suitable drying agent which is in contact with the said atmosphere. For example, a saturated solution of magnesium chloride, a saturated solution of sodium iodide or a saturated solution of potassium carbonate is employed as a drying agent, for a time sufficient to equilibrate the wet crystalline acetone solvate of the present invention with the atmosphere provided by the presence of the drying agent. Storage in the presence of a concentrated potassium carbonate solution is preferred.

During subjecting the preferably crystalline acetone solvate to said atmosphere according to d-i) or d-ii), it is possible to suitably seed the mixture. It was found, however, that seeding is not necessary. Therefore, the present invention also relates to above-described process, wherein neither in d-i) nor in d-ii), a seeding material is added.

As described above, the compound recovered in c) is subjected to stage d), preferably either subjected to drying according to d-i) or subjected to an atmosphere having a suitable relative humidity according to d-ii). Most preferably, neither before nor during c), and neither before nor during d), in particular neither before nor during d-i) and neither before nor during d-ii), an ICH class 2 solvent is employed in the process of the present invention. In particular, no solvent selected from the group consisting of acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidone, nitromethane, pyridine, sulfolane, tetrahydrofuran, tetralin, toluene, 1,1,2-trichloroethene, xylene and a mixture of two or more thereof is employed. Even more preferably, the compound recovered in c), after c), is only brought into contact with the atmosphere described above which is a mixture of air and water vapor. Therefore, the inventive process allows for preparing a crystalline compound of formula (I) at least partially, preferably essentially completely having crystalline form delta-d and/or delta, preferably delta, which compound has a very low content of, and which preferably is essentially free of, acetonitrile, in particular essentially free of an ICH class 2 solvent.

General Inventive Preparation of a Crystalline Compound of Formula (I) Having Form Delta The process as described above relates to an embodiment according to which the acetone solvate which is used as starting material for the preparation of a crystalline compound of formula (I) at least partially having crystalline form delta-d or delta, preferably delta, is prepared by a process comprising stages a) to c) as described hereinabove. However, the present invention is not restricted to this process comprising stages a) to c) and d), in particular stages a) to c) and either d-i) or d-ii), and to the crystalline compounds obtained therefrom.

The present invention generally also relates to a process wherein an acetone solvate of the compound of formula (I) is converted to a crystalline compound of formula (I) at least partially, preferably essentially completely, having polymorphic form delta. According to this general process, it is preferred that the acetone solvate used as starting material is a crystalline acetone solvate. More preferably, it is a crystalline acetone solvate having the monoclinic unit cell parameters and/or, preferably and, the acetone contents as described above, and further, having an ICH class 2 solvent content as described above. Further according this preferred embodiment of the present invention which is directed to the preparation of polymorphic form delta of the compound of formula (I), the acetone solvate employed as starting material is subjected to an atmosphere having a suitable relative humidity allowing for obtaining polymorphic form delta. Preferably, the relative humidity of said atmosphere is in the range of up to 60%, more preferably up to 50%, more preferably in the range of from 10 to 50%, more preferably of from 20 to 50%, even more preferably of from 30 to 50%. More preferably, the relative humidity is in the range of from 40 to 50% such as in the range of from 40 to 45%, 41 to 46%, 42 to 47%, 43 to 48%, 44 to 49%, or 45 to 50%.

Therefore, the present invention relates to a process for the preparation of a crystalline compound of formula (I)

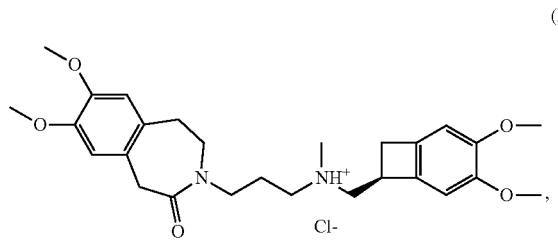

(I)

said compound at least partially, preferably essentially completely having polymorphic form delta, said process comprising subjecting a preferably crystalline acetone solvate of the compound of formula (I), to an atmosphere having a relative humidity in the range of from up to 50%, preferably from 30 to 50%, more preferably from 40 to 50%.

More preferably, the preferably crystalline acetone solvate employed as starting material has the monoclinic unit cell parameters and/or, preferably and, the acetone contents as described above, and further, having an ICH class 2 solvent content as described above.

Therefore, the present invention, according to an especially preferred embodiment, relates to a process for the preparation of a crystalline compound of formula (I)

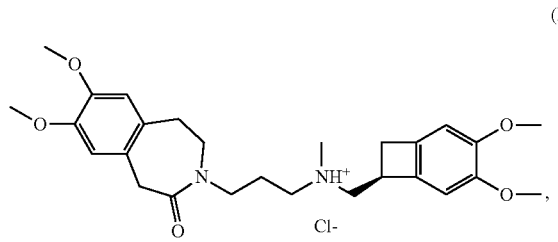

(I)

said compound at least partially, preferably essentially completely having polymorphic form delta, said process comprising subjecting a crystalline acetone solvate of the compound of formula (I) comprising acetone in the range of from 0.8 to 1.1 mol, per mol of the compound of formula (I), having an ICH class 2 solvent content of less than 5 ppm and exhibiting monoclinic unit cells having space group $P2_1$ and having the parameters a=5.72+/−0.05 Angstrom, b=11.82+/−0.05 Angstrom, c=22.03+/−0.05 Angstrom, alpha=90.0°, beta=93.2+/−0.1°, gamma=90° as determined by X-ray structural analysis, to an atmosphere having a relative humidity in the range of from up to 50%, preferably from 30 to 50%, more preferably from 40 to 50%.

The term "at least partially having crystalline form delta" as used in this context of the present invention refers to a crystalline compound of formula (I) wherein more than 50% of the crystalline compound are present in the delta form.

The term "essentially completely having crystalline form delta" as used in this context of the present invention refers to a crystalline compound of formula (I) wherein at least 90%, more preferably at least 95%, more preferably at least 99%, more preferably at least 99.9% of the crystalline compound are present in the delta form. In particular, the term "essentially completely having crystalline form delta" as used in this context of the present invention refers to an embodiment where the polymorphic form delta is the only detectable crystalline form of the compound of formula (I). The polymorphic form delta is defined with respect to its crystalline structure, for example, in US 2009/0318419 A1, in the table of page 1, right column.

The term "relative humidity" as used in this context of the present invention describes the amount of water vapor in a mixture of air and water vapor. It is defined as the partial pressure of water vapor in the air-water mixture, given as a percentage of the saturated vapor pressure under those conditions.

Preferably, subjecting the acetone solvate to said atmosphere is performed at a temperature in the range of from 15 to 35° C., more preferably of from 20 to 30° C., such as in the range of from 20 to 25° C. or of from 22 to 27° C. or of from 25 to 30° C. The preferred pressure, at these temperatures, is preferably in the range of from 0.9 to 1.1 bar, more preferably in the range of from 0.95 to 1.05 bar, more preferably in the range of from 0.98 to 1.02 bar.

Therefore, in a preferred embodiment the present invention also relates to above-described process, wherein subjecting said preferably crystalline acetone solvate to said atmosphere is performed at a temperature in the range of from 20 to 30° C. at ambient pressure.

As to the period of time within which the preferably crystalline acetone solvate is subjected to said atmosphere, a range of from 1 d to 10 d is preferred. More preferably, subjecting said preferably crystalline acetone solvate to said atmosphere is performed for a time in the range of from 2 d to 8 d, more preferably of from 72 h to 168 h, more preferably of from 72 h to 120 h.

Therefore, in a preferred embodiment, the present invention also relates to above-described process, wherein subjecting said preferably crystalline acetone solvate to said atmosphere is performed for a time in the range of from 72 h to 168 h.

Subjecting the preferably crystalline acetone solvate to said atmosphere can be done in drying chambers capable of controlling the temperature and relative humidity therein, which are commercially available. A constant climate chamber can function as a drying chamber within the meaning of this invention.

Alternatively, this subjecting step can be performed by storing the crystalline acetone solvate of the present invention at 25° C. in a dessicator in the presence of a saturated solution of magnesium chloride, sodium iodide or potassium carbonate for a time sufficient to equilibrate the wet crystalline acetone solvate of the present invention with the defined atmosphere of the dessicator. Storage in the presence of a concentrated potassium carbonate solution is preferred, as this is expected to provide an equilibrium relative humidity of about 43%.

As far as the relative humidity is concerned to which the preferably crystalline acetone solvate is subjected, the range of from 41 to 45% is especially preferred. As far as the temperature is concerned under which the preferably crystalline acetone solvate is subjected to said atmosphere, the range of from 20 to 25° C. is especially preferred. As far as the period of time is concerned within which the preferably crystalline acetone solvate is subjected to said atmosphere, the range of from 73 to 120 h is especially preferred.

Therefore, the present invention also relates to above-described process, wherein subjecting said preferably crystalline acetone solvate to said atmosphere is performed at a temperature in the range of from 20 to 25° C. at ambient pressure for a time in the range of from 72 to 120 h, wherein the relative humidity of the atmosphere is in the range of from 41 to 45%, and wherein, according to an even more preferred embodiment, said crystalline acetone solvate of the compound of formula (I) comprises acetone in the range of from 0.8 to 1.1 mol per mol of the compound of formula (I), has an ICH class 2 solvent content of less than 5 ppm and exhibits monoclinic unit cells having space group $P2_1$ and having the parameters a=5.72+/−0.05 Angstrom, b=11.82+/−0.05 Angstrom, c=22.03+/−0.05 Angstrom, alpha=90.0°, beta=93.2+/−0.1°, gamma=90° as determined by X-ray structural analysis.

Preferably, neither before said subjecting nor after said subjecting, an ICH class 2 solvent is employed in the process of the present invention. In particular, no solvent selected from the group consisting of acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidone, nitromethane, pyridine, sulfolane, tetrahydrofuran, tetralin, toluene, 1,1,2-trichloroethene, xylene and a mixture of two or more thereof is employed. Even more preferably, the preferably crystalline acetone solvate is only brought into contact with the atmosphere described above which is a mixture of air and water vapor. Therefore, the inventive process allows for preparing a crystalline compound of formula (I) at least partially, preferably essentially completely having crystalline form delta, which compound has a very low content of, and which preferably is essentially free of, acetonitrile, in particular any ICH class 2 solvent.

During subjecting the preferably crystalline acetone solvate to said atmosphere, it is possible to suitably seed the mixture. It was found, however, that seeding is not necessary to prepare the inventive crystalline compound of formula (I) at least partially, preferably essentially completely having polymorphic form delta. Therefore, the present invention also relates to above-described process, wherein for preparing the crystalline compound of formula (I), no seeding material is added.

Inventive Crystalline Compounds of Formula (I) Having Crystalline Form Delta-d or Delta From the processes as described above, in particular from the process for the preparation of a crystalline compound of formula (I) having form delta and/or delta-d according to a process comprising stages a) to c) and d-i) or d-ii), and from the general inventive process for the preparation of a crystalline compound of formula (I) having form delta, a crystalline compound of formula (I) is obtained which, as described above, preferably has at least partially, preferably essentially completely crystalline form delta-d and/or delta. Due to the use of the acetone solvate from which the crystalline compound of formula (I) is prepared, and due to the fact that the inventive process allows for avoiding ICH class 2 solvents, such as acetonitrile, it is possible to prepare crystalline compounds to have a very low respective content of these ICH class 2 solvents, such as acetonitrile. Generally, the crystalline compound of formula (I) at least partially, preferably essentially completely having crystalline form delta-d and/or delta, preferably delta, have an ICH class 2 solvent content of at most 500 ppm, preferably at most 200 ppm, more preferably less than 200 ppm, more preferably at most 20 ppm, more preferably of less than 20 ppm, more preferably at most 5 ppm, more preferably of less than 5 ppm. Preferably they have an acetonitrile content of at most 200 ppm, more preferably less than 200 ppm, more preferably at most 20 ppm, more preferably of less than 20 ppm, more preferably at most 5 ppm, more preferably of less than 5 ppm.

Therefore, the present invention relates to a crystalline compound of formula (I)

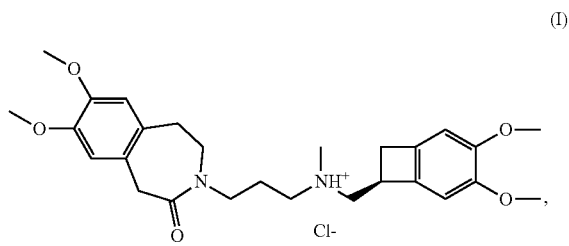

(I)

at least partially, preferably essentially completely having crystalline form delta-d and/or delta, preferably delta, said crystalline compound having an acetonitrile content, preferably an ICH class 2 solvent content of less than 200 ppm, preferably of less than 20 ppm, more preferably of less than 5 ppm. Preferably they have an acetonitrile content of at most 200 ppm, more preferably less than 200 ppm, more preferably at most 20 ppm, more preferably of less than 20 ppm, more preferably at most 5 ppm, more preferably of less than 5 ppm.

Further, the crystalline compound of formula (I) of the present invention which at least partially, preferably essentially completely has crystalline form delta-d and/or delta, preferably delta, preferably has a water content in the range of up to 15 weight-%, more preferably of up to 12 weight-%, more preferably of up to 9 weight %, the acetone content preferably being less than or equal to 0.5 weight-%, more preferably of less than or equal to 0.4 weight-%, more preferably of less than or equal to 0.3 weight-%, more preferably of less than or equal to 0.2 weight-%, more preferably of less than or equal to 0.1 weight-%, more preferably of less than or equal to 0.05 weight-%. Thus, the present invention provides, as yet another advantage, a process which allows for the preparation of a crystalline compound of formula (I) either having form delta and/or delta-d, preferably delta, which compound easily meets the ICH guideline for a class 3 solvents, due to the fact that the acetone content is, in each case, preferably less than 0.5 weight-%.

Therefore, the present invention also relates the above-described crystalline compound, having an acetone content of less than or equal to 0.5 weight-%, preferably less than or equal to 0.1 weight-%, more preferably less than or equal to 0.05 weight-%, and having a water content of up to 9 weight-%, preferably in the range of from 7.5 to 9 weight-%, more preferably from 7.5 to 8.5 weight-%.

Yet further, the present invention relates to said crystalline compounds of formula (I) wherein said compounds are obtainable or obtained by the above-described process, most preferably by a process wherein a crystalline acetone solvate of the compound of formula (I) is subjected to an atmosphere having a relative humidity in the range of from 41 to 45%, said subjecting being performed at a temperature in the range of from 20 to 25° C. at ambient pressure for a time in the range of from 72 to 120 h, wherein before, during or after said subjecting, exclusively an atmosphere of gaseous water in air is brought into contact with the crystalline acetone solvate of the compound of formula (I), and wherein, preferably, said crystalline acetone solvate of the compound of formula (I) comprises acetone in the range of from 0.8 to 1.1 mol per mol of the compound of formula (I), has an ICH class 2 solvent content of less than 5 ppm and exhibits monoclinic unit cells having space group $P2_1$ and having the parameters a=5.72+/−0.05 Angstrom, b=11.82+/−0.05 Angstrom, c=22.03+/−0.05 Angstrom, alpha=90.0°, beta=93.2+/−0.1°, gamma=90° as determined by X-ray structural analysis.

Subjecting the crystalline acetone solvate to said atmosphere can be done in drying chambers capable of controlling the temperature and relative humidity therein, which are commercially available. Alternatively, this subjecting step can be performed by storing the crystalline acetone solvate of the present invention at 25° C. in a dessicator for a period of time as described above in the presence of a concentrated potassium carbonate solution, as this is expected to provide an equilibrium relative humidity of about 43%.

Pharmaceutical Compositions and Containers Containing the Compositions

The crystalline compound of formula (I) essentially having polymorphic form delta as described above may advantageously be employed in various pharmaceutical formulations as, for example, a cardiotonic agent.

The present invention therefore relates to a pharmaceutical composition which comprises the inventive crystalline compound of formula (I) having polymorphic form delta and at least one pharmaceutically acceptable excipient. Further, the present invention relates to the inventive crystalline compound of formula (I) having polymorphic form delta, comprised in a pharmaceutical composition.

As pharmaceutically acceptable excipient, the pharmaceutical composition according to the present invention may comprise one excipient or a combination of two or more excipients selected from the group consisting of fillers, sweeteners, buffering agents, glidants, flowing agents, flavouring agents, lubricants, preservatives, surfactants, wetting agents, binders, disintegrants and thickeners. Preferred pharmaceutical compositions may comprise from 2 to 10 mg, preferably from 3 to 9 mg, more preferably from 4 mg to 8 mg of the compound of formula (I), calculated as free base, and further, as pharmaceutically acceptable excipients, for example lactose monohydrate, magnesium stearate, maize starch, maltodextrin, colloidal silica (anhydrous) as core, in case, for example, the pharmaceutical composition is in the form of a tablet, and as coating agents, for example hypromellose, titanium dioxide, macrogol 6000, glycerole, magnesium stearate, yellow and red iron oxide.

In order to stabilize the polymorphic form delta of the compound of formula (I) present in such pharmaceutical composition, it was found that preferably, this pharmaceutical composition exhibits an equilibrium relative humidity of about 30% to about 50%, preferably in the range of from 30 to 50% determined according to the ERH method. For such pharmaceutical compositions, it is envisaged that the polymorphic form delta of the compound of formula (I) is polymorphically stable for an extended period of time, such as for a time of at least 180 days, preferably at least 2 years, if kept at storage conditions which assure that the equilibrium relative humidity of the pharmaceutical composition remains in the range of about 30% to about 50%. One way to achieve this is, for example, to store the pharmaceutical composition under an atmosphere of about 30% to about 50% relative humidity, for example in drying chambers capable of controlling the temperature and relative humidity therein. Alternatively, storage can be in the presence of a concentrated potassium carbonate solution in an otherwise closed container.

The term "polymorphically stable" as used in this context of the present invention relates to a pharmaceutical composition comprising polymorphic form delta of the compound of formula (I), wherein at least 90%, more preferably at least 95% of the compound of formula (I) comprised in the composition and having polymorphic form delta are stably present as polymorphic form delta for an extended period of time, preferably for at least 180 d, more preferably for at least 2 years.

Therefore, the present invention relates to above-described pharmaceutical composition, having an equilibrium relative humidity in the range of from 30 to 50% at a temperature of the composition in the range of from 20 to 30° C.

Further, the present invention relates to an above-described pharmaceutical composition, wherein at least 90%, more preferably at least 95% of the compound of formula (I) comprised in the composition and having polymorphic form delta are stably present as polymorphic form delta.

In particular, the present invention relates to the above-described pharmaceutical composition, wherein at least 90%, more preferably at least 95% of the compound of formula (I) comprised in the composition and having polymorphic form delta are stably present as polymorphic form delta, which pharmaceutical composition is to be kept at storage conditions which assure that the equilibrium relative humidity of the pharmaceutical composition remains in the range of about 30% to about 50%. One way to achieve this is, for example, to add instructions to the pharmaceutical composition that it should be stored under an atmosphere of about 30% to about 50% relative humidity, for example in a drying chamber capable of controlling the temperature and relative humidity therein.

The ERH Method

The equilibrium relative humidity of a pharmaceutical composition as referred to in the context of the present invention is measured by determining the relative humidity in % in the air above a test sample, for example a pharmaceutical composition of the present invention, after establishment of a humidity equilibrium in a closed system at a constant temperature according to the following method: the equipment used is the commercially available measuring chamber Rotronic AW-VC comprising a hygrometer of the type BT-RS1. The test sample is filled into a sampling dish which is placed into the measuring chamber which is thermostatically controlled and kept at a temperature of 25+/−1° C. Said chamber is subsequently closed and sealed. After establishment of equilibrium of the relative humidity which state is typically shown by the disappearance of a trend indication, the value of the relative humidity in % is read from the hygrometer. Relative humidity is defined as the equilibrium relative humidity of the pharmaceutical compositions as measured as herein described. Filling of the chamber is to be performed in such a way as to provide complete filling of said chamber according to the instructions of the manufacturers. In case the test sample is a powder or granules for oral suspension, or a liquid suspension, said sample is directly placed into the above mentioned sampling dish. In case the test sample is a capsule, the appropriate number of capsules is opened and their contents are filled into the sampling dish. In case the test sample is a tablet, the appropriate number of tablets is crushed by using a mortar, and filled into the sampling dish. In cases where the equilibrium relative humidity is expected to be in the range of from 30 to 50%, the above described preparation of the test samples before measurement and the measurement itself as herein described is to be performed in a glove box being equipped with a hygrometer wherein a relative humidity of about 5% is to be established by e.g. flushing with dried air or nitrogen. The above described method for measurement of the equilibrium relative humidity of the pharmaceutical compositions of the invention is herein also called ERH method.

In order to stabilize the delta form of the compound of formula (I) in case said compound is comprised in a pharmaceutical composition, it is possible to expose the pharmaceutical composition to an atmosphere having a relative humidity in the range of from 30 to 50% for an extended period of time. Preferably, such exposing is accomplished by using a container comprising the pharmaceutical composition, which container is either capable of maintaining the atmosphere to which the pharmaceutical composition is exposed at a relative humidity in the range of from 30 to 50% or is equipped with means allowing for maintaining the atmosphere to which the pharmaceutical composition is exposed at a relative humidity in the range of from 30 to 50%.

Therefore, the present invention also relates to the above-described pharmaceutical composition, comprised in a container, preferably in a container capable of maintaining the atmosphere to which the pharmaceutical composition is exposed at a relative humidity in the range of from 30 to 50%, preferably for an extended period of time, more preferably for at least 180 d, even more preferably of at least 2 years.

A container capable of maintaining the atmosphere to which the pharmaceutical composition is exposed at a relative humidity in the range of from 30 to 50% is, for example, a container prepared from a material having a permeability for water vapor as measured according to DIN 53 122 at a foil thickness of 50 μm of below 0.05 $g*m^{-2}*d^{-1}$, such as a sealed metal container, for example a tightly sealed aluminum-aluminum blister.

Alternatively, the present invention also relates to the above-described pharmaceutical composition, comprised in a container, preferably in a container containing means for maintaining the atmosphere to which the pharmaceutical composition is exposed at a relative humidity in the range of from 30 to 50%, preferably for an extended period of time, more preferably for at least 180 d, more preferably of at least 2 years.

Such a container is, for example, a constant climate chamber as commercially available, for example the climate chamber HPP108 available from Memmert, Schwabach, Germany.

Also, the present invention relates to said container as such, i.e. a container capable of maintaining the atmosphere to which the pharmaceutical composition is exposed at a relative humidity in the range of from 30 to 50% is, preferably for an extended period of time, more preferably for at least 180 d, more preferably for at least 2 years. Such a container can be prepared from a material having a permeability for water vapor as measured according to DIN 53 122 at a foil thickness of 50 μm of below 0.05 $g*m^{-2}*d^{-1}$, and can be a sealed metal container, for example a tightly sealed aluminum-aluminum blister.

In a preferred embodiment, the present invention relates to a container comprising a pharmaceutical composition according to the below embodiments I, II and/or III, the container being capable of maintaining the atmosphere to which the pharmaceutical composition is exposed at a relative humidity in the range of from 30 to 50% for at least 180 d, wherein the container is an aluminum-aluminum blister and wherein at least 95% of the crystalline compound of formula (I) are in the form of crystalline form delta, in particular wherein said container comprising the pharmaceutical composition according to embodiments I, II and/or III is intended for use in a country comprising areas with a BWh or BWk or BWn climate according to the Koppen-Geiger climate classification Further, the present invention also relates to the following embodiments, including all combinations of the embodiments resulting from the specific back-references explicitly contained in the embodiments:

I. A pharmaceutical composition, comprising a crystalline compound of formula (I)

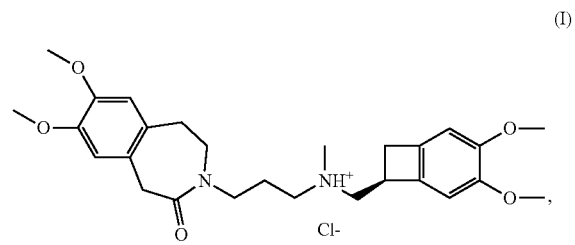

at least partially, preferably essentially completely having crystalline form delta, said crystalline compound having an acetonitrile content, preferably an ICH class 2 solvent content of less than 200 ppm, preferably of less than 20 ppm, more preferably of less than 5 ppm, having an acetone content of less than or equal to 0.5 weight-%, preferably less than or equal to 0.1 weight-%, more preferably less than or equal to 0.05 weight-%, and having a water content in the range of from 7.5 to 9 weight-%, more preferably from 7.5 to 8.5 weight-%, said pharmaceutical composition further comprising at least one pharmaceutically acceptable excipient, wherein the pharmaceutical composition has an equilibrium relative humidity in the range of from 30 to 50% determined according to the ERH method.

II. The pharmaceutical composition of embodiment I, wherein at least 90%, preferably at least 95% of the crystalline form delta of the compound of formula (I) are polymorphically stable for an extended period of time, preferably for a time of at least 180 d, more preferably at least 2 years.

III. The pharmaceutical composition of embodiment I or II in oral dosage form, preferably in the form of a tablet or a capsule, more preferably a tablet.

IV. The pharmaceutical composition of any of embodiments I to III, comprised in a container, preferably in a container containing means for keeping the equilibrium relative humidity of the pharmaceutical composition in a range of from 30 to 50% determined according to the ERH method, for an extended period of time, preferably for a time of at least 180 d, more preferably at least 2 years.

V. The pharmaceutical composition of embodiment IV, wherein the pharmaceutical composition comprised in the container is for use in a country comprising areas with a BWh or BWk or BWn climate according to the Koppen-Geiger climate classification.

VI. A process for the preparation of the pharmaceutical composition of any of embodiments I to V, comprising
  i. mixing the crystalline compound of formula (I), said crystalline compound at least partially, preferably essentially completely having polymorphic form delta, with one or more pharmaceutically acceptable excipients at a relative humidity in the range of from 30 to 50%;
  ii. optionally granulating the mixture obtained in i. at a relative humidity in the range of from 30 to 50%;
  iii. further processing the mixture obtained in i. or the granulate obtained in ii. at a relative humidity in the range of from 30 to 50% to obtain the pharmaceutical composition.
VII. The process of embodiment VI, wherein the mixture or the granulate is further processed in iii. into an oral dosage form, preferably a tablet or a capsule, more preferably a tablet.
VIII. The process of embodiment VI or VII, further comprising
  iv. filling the obtained pharmaceutical composition having an equilibrium relative humidity in the range of from 30 to 50% determined according to the ERH method into a container equipped with means allowing for keeping the equilibrium relative humidity of the pharmaceutical composition in said range for an extended period of time, preferably for at least 180 d, more preferably for at least 2 years.
IX. A container comprising a pharmaceutical composition according to any of embodiments I to III or a pharmaceutical composition obtainable or obtained according to a process of any of embodiments VI to VIII, said container being capable to maintain or equipped with means allowing for keeping the equilibrium relative humidity of the pharmaceutical composition in a range of from 30 to 50% determined according to the ERH method.
X. The container of embodiment IX, wherein the pharmaceutical composition comprised therein is for use in a country comprising areas with a BWh or BWk or BWn climate according to the Koppen-Geiger climate classification.
XI. Use of an atmosphere having a relative humidity in the range of from 30 to 50% for polymorphically stabilizing the crystalline form delta of the compound of formula (I)

(I)

XII. The pharmaceutical composition of any of embodiments I to V which is to be stored at a relative humidity in the range of from 30 to 50%, in particular also intended for use in a country comprising areas with a BWh or BWk or BWn climate according to the Koppen-Geiger climate classification.

The present invention is further described by reference to the following examples. These examples are provided for illustration purposes only and are not intended to be limiting the present invention in any way.

EXAMPLES

Example 1

Acetone Solvate of Ivabradine Hydrochloride from Form Alpha of Ivabradine Hydrochloride Ivabradine hydrochloride (0.10 g, form alpha) was suspended in 4 ml acetone (p.a.) and stirred for 1 hour. After filtration the suspension, ivabradine hydrochloride (0.10 g; form acetone solvate) was obtained. Yield: 94% of the theory.

The sample was stored under an atmosphere of acetone

Example 2

Acetone Solvate of Ivabradine Hydrochloride from Form Beta of Ivabradine Hydrochloride Ivabradine hydrochloride (0.10 g, form beta) was suspended in 4 ml acetone (p.a.) and stirred for 1 hour and was then stored in the refrigerator (2° C.-8° C.). over night. After filtration the suspension, ivabradine hydrochloride (0.09 g; form acetone solvate) was obtained. Yield: 94% of the theory.

Example 3

Acetone Solvate of Ivabradine Hydrochloride from Form Delta of Ivabradine Hydrochloride Ivabradine hydrochloride (0.06 g, form delta) was suspended in 4 ml acetone (p.a.) and stirred for 1 hour. After filtration the suspension, ivabradine hydrochloride (0.06 g; form acetone solvate) was obtained. Yield: 94% of the theory.

Example 4

Acetone Solvate of Ivabradine Hydrochloride from Form Delta-d of Ivabradine Hydrochloride Ivabradine hydrochloride (0.12 g, form delta-d) was suspended in 4 ml acetone (p.a.) and stirred for 1 hour and was then stored in the fridge overnight. After filtration the suspension, ivabradine hydrochloride (0.12 g; form acetone solvate) was obtained. Yield: 94% of the theory.

Example 5

Preparation of Ivabradine Hydrochloride Form Delta from the Acetone Solvate of Ivabradine Hydrochloride Ivabradine hydrochloride (1.00 g; form acetone solvate) was stored in an aluminium pan at 45% relative humidity at ambient temperature (over saturated calcium carbonate solution). After 72 hours, ivabradine hydrochloride (0.89 g; form delta) was obtained. The confirmation of the presence of form delta was performed by PXRD analysis. Yield: 99% of the theory.

Residual acetone was not detectable by $^1$H-NMR (dmso-d$_6$).

Example 6

Preparation of Ivabradine Hydrochloride Form Delta-d from Crystalline Acetone Solvate of Ivabradine Hydrochloride Ivabradine hydrochloride (1.00 g, form acetone solvate) was dried in a vial in vacuo at 70° C. for 14 hours. Ivabradine hydrochloride (0.89 g, form delta-d) was obtained.

Identification of the form delta-d was performed by PXRD. Yield: 99% of the theory. The acetone content ($^1$H-NMR, dmso-$d_6$) was less than 0.5 weight %.

Example 7

Analysis of the Acetone Solvate of Ivabradine Hydrochloride Prepared According to the Present Invention Intensity data for the crystal structure of the acetone solvate were collected with Cu (lambda=1.5418 Angstrom) radiation on an Oxford Diffraction Gemini-R Ultra diffractometer, which was operated by the CrysAlis software. The structure was solved using the direct methods procedure in SHELXS97 and refined by full-matrix least squares on $F^2$ using SHELXL97. All non-hydrogen atoms were refined anisotropically. A summary of the basic crystal data is given in Table 1 below. The atomic coordinates and equivalent isotropic displacement parameters are shown in Table 2 below.

TABLE 1

Crystal data and structure refinement of the crystalline acetone solvate of ivabradine hydrochloride

| | |
|---|---|
| Empirical formula | $C_{29.80}H_{42.59}ClN_2O_{5.93}$ |
| Moiety formula | $C_{27}H_{36}N_2O_5 \cdot HCl \cdot 0{,}93$ $(C_3H_6O)$ |
| Formula weight | 559.12 for $C_{27}H_{36}N_2O_5 \cdot HCl \cdot 0{,}93$ $(C_3H_6O)$ (505.05 for $C_{27}H_{36}N_2O_5 \cdot HCl$) |
| Temperature | 173(2) K |
| Wavelength | 1.54180 Angstrom |
| Crystal system | Monoclinic |
| Space group | $P2_1$ |
| Unit cell dimensions | a = 5.7195(4) Angstrom |
| | b = 11.8231(4) Angstrom |
| | c = 22.0254(12) Angstrom |
| | alpha = 90°. |
| | beta = 93.182(5)°. |
| | yamma = 90°. |
| Volume | 1487.11(14) Angstrom$^3$ |
| Z | 2 |
| Density (calculated) | 1.249 Mg/m$^3$ |
| Crystal size | 0.40 × 0.36 × 0.04 mm$^3$ |
| Theta range for data collection | 4.02 to 67.39°. |
| Index ranges | $-6 \leq h \leq 5$, $-6 \leq k \leq 14$, $-23 \leq l \leq 24$ |
| Reflections collected | 5224 |
| Independent reflections | 2701 [$R_{(int)}$ = 0.0262] |
| Completeness to theta = 67.39° | 76.2% |
| Absorption correction | Semi-empirical from equivalents |
| Data/restraints/parameters | 2701/1/364 |
| Goodness-of-fit on $F^2$ | 1.040 |
| Final R indices [I > 2sigma(I)] | R1 = 0.0355, wR2 = 0.0975 |
| R indices (all data) | R1 = 0.0364, wR2 = 0.0991 |
| Absolute structure parameter | 0.009(17) |
| Largest diff. peak and hole | 0.283 and −0.164 e. Angstrom$^{-3}$ |

TABLE 1

Atomic coordinates (× 10$^4$) for ivabradine hydrochloride acetone solvate

| atom | x | y | z |
|---|---|---|---|
| Cl(1) | 10900(1) | 7760(1) | −192(1) |
| O(30) | 11253(5) | 9134(2) | 4730(1) |
| N(15) | 5972(4) | 4771(2) | 402(1) |
| O(26) | 4529(5) | 5936(2) | −3106(1) |
| O(31) | 14384(5) | 7541(2) | 4657(1) |
| O(27) | 1540(5) | 7085(2) | −2539(1) |
| O(34) | 11923(5) | 6164(3) | 1721(1) |
| N(9) | 8457(5) | 6981(2) | 1899(1) |
| C(21) | 7890(7) | 4925(3) | −960(2) |
| C(6) | 9374(6) | 8595(3) | 3756(2) |
| C(13) | 6462(6) | 6730(2) | 873(2) |
| C(22) | 3241(6) | 6576(3) | −1539(2) |
| C(16) | 4635(6) | 5197(3) | −158(1) |
| C(19) | 5021(6) | 5957(3) | −1241(2) |
| C(18) | 6179(6) | 5718(3) | −613(2) |
| C(32) | 16021(7) | 6635(4) | 4642(2) |
| C(8) | 10419(7) | 6410(3) | 2078(2) |
| C(24) | 4806(7) | 5884(3) | −2480(2) |
| C(14) | 7620(6) | 5619(2) | 706(1) |
| C(11) | 7300(7) | 8135(3) | 2769(2) |
| C(12) | 8132(7) | 7434(3) | 1284(2) |
| C(10) | 6635(7) | 7202(3) | 2323(2) |
| C(28) | 18(7) | 7844(4) | −2249(2) |
| C(20) | 6588(6) | 5311(3) | −1540(2) |
| C(2) | 12689(7) | 7596(3) | 4187(2) |
| C(7) | 10708(7) | 6068(3) | 2738(2) |
| C(33) | 9297(8) | 9839(4) | 4840(2) |
| C(25) | 6563(7) | 5262(3) | −2166(2) |
| C(23) | 3157(6) | 6526(3) | −2168(2) |
| C(1) | 11051(7) | 8460(3) | 4223(2) |
| C(5) | 9214(6) | 7867(3) | 3248(2) |
| C(3) | 12557(7) | 6872(3) | 3692(2) |
| C(29) | 6380(8) | 5457(4) | −3433(2) |
| C(17) | 4327(6) | 4280(3) | 833(2) |
| C(4) | 10806(6) | 6986(3) | 3223(2) |
| O(36) | 8093(12) | 4647(4) | 3691(2) |
| C(35) | 7211(13) | 3739(5) | 3779(2) |
| C(38) | 8544(11) | 2767(7) | 3991(2) |
| C(37) | 4704(15) | 3554(6) | 3761(5) |

Literature Cited

US 7,384,932
US 7,867,997
ICH Steering Committee , Guideline for Residual Solvents, 17.07.1997
WO 2008/146308
WO 2005/110993
WO 2006/092493
WO 2006/092491
WO 2006/092492
WO 2006/092494
WO 2007/042656
WO 2007/042657
US 2007/0082886 A1
US 2009/0318419 A1

The invention claimed is:
1. A crystalline acetone solvate of the compound of formula (I)

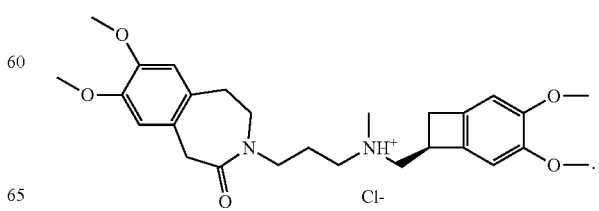

(I)

2. The acetone solvate of claim 1, comprising acetone in the range of from 0.7 to 1.1 mol per mol of the compound of formula (I).

3. The acetone solvate of claim 1, exhibiting monoclinic unit cells having space group P2$_1$ and having the parameters
a=5.72+/−0.05 Angstrom
b=11.82+/−0.05 Angstrom
c=22.03+/−0.05 Angstrom
alpha=90.0°
beta=93.2+/−0.1°
gamma=90°
as determined by X-ray structural analysis.

4. A process comprising
a) providing a crystalline compound of formula (I)

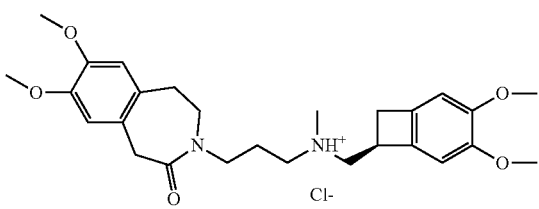
(I)

or a solvate, other than an acetone solvate, thereof, wherein the crystalline compound of formula (I) is provided as crystalline form alpha, or beta, or beta-d, or gamma, or gamma-d, or delta, or delta-d, or as a mixture of two or more of these crystalline forms;
b) combining the compound provided in a) with acetone at a temperature in the range of from 0 to 30° C. and crystallizing the acetone solvate for a time in the range of from 1 to 48 h and at a temperature in the range of from 0 to 30° C.;
c) recovering a crystalline acetone solvate of the compound of formula (I).

5. The process of claim 4, wherein in b), combining and crystallizing is performed at a temperature in the range of from 20 to 30° C., or wherein in b), combining is performed at a temperature in the range of from 20 to 30° C. and crystallizing is performed according to a method comprising
(i) stirring the compound provided in a) combined with the acetone for a time in the range of from 0.5 to 6 h and at a temperature in the range of from 20 to 30° C.;
(ii) keeping the mixture obtained from (i) for a time in the range of from 0.5 to 42 h at a temperature in the range of from 0 to 10° C.

6. The process of claim 4, wherein before or during b), the compound provided in a) is combined with no compound other than acetone.

7. The process of claim 4, further comprising
d-i) drying the crystalline acetone solvate recovered in c), wherein a crystalline compound of formula (I) is obtained, at least partially, having crystalline form delta-d, said drying being performed at a temperature in range of from 20 to 100° C., in vacuo; or
d-ii) subjecting the crystalline acetone solvate recovered in c) to an atmosphere having a relative humidity up to 50%, wherein a crystalline compound of formula (I) is obtained, at least partially having crystalline form delta, said subjecting according to d-ii) being performed at a temperature in the range of 20 to 30° C. and for a time in the range of from 72 to 168 h.

8. A process for the preparation of a crystalline compound of formula (I)

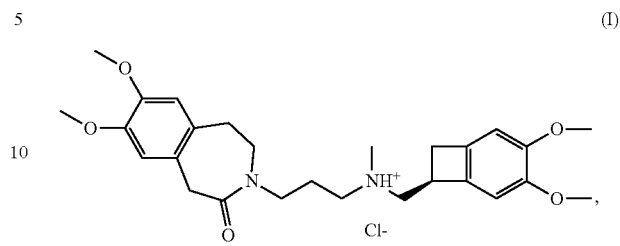
(I)

said compound at least partially having polymorphic form delta, said process comprising subjecting a crystalline acetone solvate of the compound of formula (I) to an atmosphere having a relative humidity up to 50%.

9. The process of claim 8, wherein subjecting said crystalline acetone solvate to said atmosphere is performed at a temperature in the range of from 20 to 30° C. at ambient pressure.

10. The process of claim 8, wherein subjecting said crystalline acetone solvate to said atmosphere is performed for a time in the range of from 72 to 168 h.

11. The process of claim 8, wherein subjecting said crystalline acetone solvate to said atmosphere is performed at a temperature in the range of from 20 to 25° C. at ambient pressure for a time in the range of from 72 to 120 h, wherein the relative humidity of the atmosphere is in the range of from 41 to 45%.

12. A crystalline compound of formula (I)

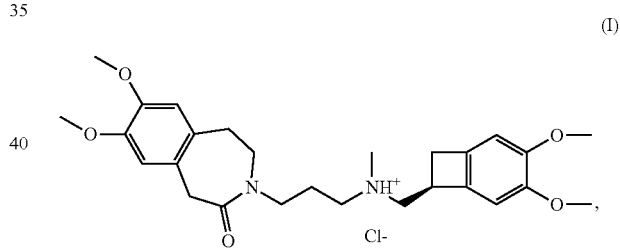
(I)

at least partially having crystalline form delta-d and/or delta, said crystalline compound having an acetonitrile content of less than 200 ppm.

13. The crystalline compound of claim 12, having an acetone content of less than or equal to 0.5 weight-%, and having a water content of up to 9 weight-%.

14. A crystalline compound, obtainable or obtained by the process according to claim 7, said crystalline compound having an acetonitrile content of less than 200 ppm.

15. A pharmaceutical composition, comprising the crystalline compound according claim 12, and at least one pharmaceutically acceptable excipient.

16. The pharmaceutical composition of claim 15, having an equilibrium relative humidity in the range of from 30 to 50% determined according to the ERH method.

17. The pharmaceutical composition of claim 15, wherein at least 90% of the compound of formula (I) comprised in the composition and having polymorphic form delta are stably present as polymorphic form delta.

18. The pharmaceutical composition of claim 15, comprised in a container containing means for keeping the equilibrium relative humidity of the pharmaceutical composition in a range of from 30 to 50% determined according to the ERH method for at least 180 d.

19. A container comprising a pharmaceutical composition according to claim 15, the container containing means for keeping the equilibrium relative humidity of the pharmaceutical composition in a range of from 30 to 50% determined according to the ERH method, for at least 180 d.

* * * * *